US008185344B2

(12) United States Patent
Troxler et al.

(10) Patent No.: US 8,185,344 B2
(45) Date of Patent: *May 22, 2012

(54) METHOD OF DETERMINING A DIMENSION OF A SAMPLE OF A CONSTRUCTION MATERIAL AND ASSOCIATED APPARATUS

(75) Inventors: Robert Ernest Troxler, Raleigh, NC (US); James Daniel Pratt, Jr., Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/128,556

(22) Filed: May 28, 2008

(65) Prior Publication Data

US 2008/0249738 A1    Oct. 9, 2008

(51) Int. Cl.
*G01B 5/00* (2006.01)
(52) U.S. Cl. ......................................................... 702/156
(58) Field of Classification Search .................. 702/156, 702/33, 155, 159, 167, 168, 171, 172; 73/105; 356/600, 601
See application file for complete search history.

(56) References Cited

U.S. PATENT DOCUMENTS

| | | | |
|---|---|---|---|
| 3,873,226 A | 3/1975 | Teach | |
| 4,238,147 A | 12/1980 | Stern | |
| 4,280,354 A | 7/1981 | Wheeler et al. | |
| 4,573,131 A * | 2/1986 | Corbin | 702/168 |
| 4,590,367 A | 5/1986 | Ross et al. | |
| 4,705,401 A | 11/1987 | Addleman et al. | |
| 4,715,717 A * | 12/1987 | Evans | 356/429 |
| 4,737,032 A | 4/1988 | Addleman et al. | |
| 4,796,998 A | 1/1989 | Soma et al. | |
| 4,895,440 A | 1/1990 | Cain et al. | |
| 4,899,296 A * | 2/1990 | Khattak | 702/40 |
| 4,946,281 A | 8/1990 | Dell'Eva et al. | |
| 4,954,962 A | 9/1990 | Evans, Jr. et al. | |
| 4,958,306 A | 9/1990 | Powell et al. | |
| 4,978,219 A | 12/1990 | Bessho | |
| 4,979,815 A | 12/1990 | Tsikos | |
| 4,989,984 A * | 2/1991 | Salinger | 356/445 |
| 5,065,618 A | 11/1991 | Hodges, Sr. et al. | |

(Continued)

FOREIGN PATENT DOCUMENTS

DE    41 35 329 A1    4/1993

(Continued)

OTHER PUBLICATIONS

"Combatting Pavement Roughness with Rosan," Focus, Oct. 2001.

(Continued)

*Primary Examiner* — Cindy H Khuu
(74) *Attorney, Agent, or Firm* — Olive Law Group, PLLC

(57) ABSTRACT

An apparatus for determining a dimension of a construction material is provided. At least one material-interacting device is configured to interact with the construction material so as to determine at least one surface characteristic thereof. A computer device is configured to be capable of receiving the at least one surface characteristic from the at least one material-interacting device, and to manipulate the at least one surface characteristic so as to form a multi-dimensional representation of the construction material. The computer device is further configured to determine the surface or volume characteristic of the construction material from the multi-dimensional representation thereof. By determining the mass of the construction material, the density of the construction material can be provided. An associated method is also provided.

36 Claims, 6 Drawing Sheets

U.S. PATENT DOCUMENTS

| | | | |
|---|---|---|---|
| 5,085,502 A | 2/1992 | Womack et al. | |
| 5,155,558 A * | 10/1992 | Tannenbaum et al. | 356/446 |
| 5,362,176 A | 11/1994 | Sovik | |
| 5,371,588 A * | 12/1994 | Davis et al. | 356/489 |
| 5,396,510 A | 3/1995 | Wilson | |
| 5,412,420 A | 5/1995 | Ellis | |
| 5,471,303 A * | 11/1995 | Ai et al. | 356/497 |
| 5,484,227 A | 1/1996 | Ikeda et al. | |
| 5,531,520 A | 7/1996 | Grimson et al. | |
| 5,546,123 A | 8/1996 | Ikeda et al. | |
| 5,570,183 A * | 10/1996 | Wiles | 356/613 |
| 5,774,374 A * | 6/1998 | Scott et al. | 702/155 |
| 5,790,243 A * | 8/1998 | Herr | 356/5.1 |
| 5,835,053 A * | 11/1998 | Davis | 342/22 |
| 5,952,561 A | 9/1999 | Jaselskis et al. | |
| 6,005,959 A | 12/1999 | Mohan et al. | |
| 6,028,672 A * | 2/2000 | Geng | 356/602 |
| 6,028,948 A | 2/2000 | Kil et al. | |
| 6,049,384 A | 4/2000 | Rudd et al. | |
| 6,061,126 A | 5/2000 | Yoshimura et al. | |
| 6,068,060 A | 5/2000 | Ohtomo et al. | |
| 6,100,537 A * | 8/2000 | Abraham et al. | 250/559.22 |
| 6,113,309 A | 9/2000 | Hollon et al. | |
| 6,230,552 B1 * | 5/2001 | Abe et al. | 73/104 |
| 6,269,197 B1 | 7/2001 | Wallack | |
| 6,310,964 B1 | 10/2001 | Mohan et al. | |
| 6,321,589 B1 | 11/2001 | Regimand | |
| 6,328,634 B1 * | 12/2001 | Shen et al. | 451/41 |
| 6,407,818 B1 | 6/2002 | Whitehouse | |
| 6,434,257 B1 | 8/2002 | Mohan et al. | |
| 6,492,641 B1 | 12/2002 | Dep et al. | |
| 6,512,239 B1 * | 1/2003 | Weiss et al. | 250/559.4 |
| 6,679,106 B1 * | 1/2004 | Sawa et al. | 73/105 |
| 7,197,425 B2 * | 3/2007 | Masuyama et al. | 702/158 |
| 2002/0180865 A1 | 12/2002 | Lee et al. | |
| 2004/0017563 A1 | 1/2004 | James et al. | |
| 2004/0090634 A1 * | 5/2004 | Mathur et al. | 356/497 |

FOREIGN PATENT DOCUMENTS

| | | |
|---|---|---|
| DE | 42 08 455 A1 | 9/1993 |
| EP | 0 595 428 A2 | 5/1994 |
| EP | 1 046 478 A1 | 10/2000 |
| EP | 1 224 421 A2 | 7/2002 |
| GB | 2 218 513 A | 11/1989 |

OTHER PUBLICATIONS http://www.perception.com/home_flash.html, Accessed Nov. 9, 2004.

"Advances in CMOSTechnology Enables Higher Speed True 3D-Measurements," Dr. Mattias Johannesson and Hakan Thorngren, Integrated Vision Products Inc., 2000.

Office Action from the Patent Office of the People's Republic of China for Chinese Patent Application No. 200480023497.3 dated Aug. 17, 2007.

Notice of Allowance for U.S. Appl. No. 10/870,682 dated Feb. 14, 2008.

Office Action for U.S. Appl. No. 10/870,682 dated Aug. 31, 2007.

Office Action for U.S. Appl. No. 10/870,682 dated Jan. 31. 2007.

Restriction/Election Requirement for U.S. Appl. No, 10/870,682 dated Aug. 2, 2006.

"Standard Test Method for Measuring Pavement Macrotexture Depth Using a Volumetric Technique," American Society for Testing and Materials (ASTM), ASTM Designatidn: E 965-96, 2000.

"Circular Texture Meter Proves Useful for Measuring Pavement Surface Texture," Douglas I. Hanson and Brian D. Prowell, available at www.eng.auburn.edu/center/ncat, Spring 2006.

Office Action from the Patent Office of the People's Republic of China for Chinese Patent Application No. 200480023497.3 dated Mar. 7, 2008.

Standard Practice for Calculating Pavement Macrotexture Mean Profile Depth, ASTM International Designation: E 1845-01 (Reapproved 2005).

Examination Report for corresponding European patent application No. 04 755 511.5-2213, Nov. 17, 2010.

* cited by examiner

METHOD OF DETERMINING A DIMENSION OF A SAMPLE OF A CONSTRUCTION MATERIAL AND ASSOCIATED APPARATUS

RELATED APPLICATIONS

The presently disclosed subject matter claims the benefit of U.S. patent application Ser. No. 10/870,682, filed Jun. 17, 2004 and now U.S. Pat. No. 7,389,199, which claims the benefit of U.S. Provisional Application No. 60/478,992, filed Jun. 17, 2003, the disclosures of which are incorporated herein by reference in their entireties.

TECHNICAL FIELD

The subject matter described herein relates to an apparatus and method for determining at least one dimension of a sample. Particularly, the subject matter described herein relates to an apparatus and method for determining at least one dimension of a sample of an uncompacted bituminous paving mixture, soil, and/or aggregate, as well as a field core, a laboratory prepared specimen of compacted bituminous paving material, and/or other construction material.

BACKGROUND

The construction industry relies on materials testing for design, quality control and quality assurance of various construction projects. Material density and specific gravity are among some of the critical parameters of materials testing. The pavement construction industry, in particular, uses material density and specific gravity in the design and quality determinations of natural and manufactured paving materials.

In the asphalt paving industry, air void contents of hot-mix asphalt laboratory prepared specimens or cored pavement specimens are used, for example, to determine the quality of the mix design, the plant-produced hot-mix, and the pavement construction. The air void content of compacted specimens is determined, in some instances, as a ratio of the actual specific gravity of the compacted specimen (bulk specific gravity) to the theoretical maximum specific gravity of the loose asphalt mixture.

The determination of the maximum specific gravity or density of the loose asphalt mixtures may have some limitations that affect the accuracy of the air void content measurement. Furthermore, methods of determining bulk specific gravity are highly operator dependent and therefore may yield highly variable results, also affecting the air void content determination. Currently, there are three generally accepted practices or methods of determining the bulk specific gravities of compacted asphalt specimens. These methods are (1) gamma attenuation; (2) applications of Archimedes' principle; and (3) dimensional analysis.

Gamma attenuation technology can be used to provide bulk density of a compacted asphalt specimen by measuring its electron density as described, for example, in U.S. Pat. No. 6,492,641 to Dep et al. The electron density is determined by the intensity and energy distribution of gamma radiation traversing the sample. The gamma radiation is typically emitted from low-level radiation cesium sources and detected by a sensitive sodium iodide detector. The resulting measurement of the electron density must then be normalized by the height (or thickness) of the specimen. However, while the electron density determination is generally precise and reliable, the gamma attenuation method may be limited by the ability of the operator to measure the height of the specimen with accuracy and precision.

ASTM D3549 is a standard test method for thickness or height determination of compacted bituminous paving mixture specimens. The standard specifies that an average of four measurements, spaced apart at 90° intervals, should be used to approximate the height of the specimen. It further suggests that ends of the specimen that are not horizontal relative to the vertical axis of the cylinder shall be sawn flat and horizontal. However, there are several problems associated with this method. For example, in some cases, the operator may not ensure that the ends of the specimen are flat and horizontal, thereby introducing error into the height measurement because the end-to-end (or peak-to-peak) caliper measurements will not be reliable height measurements of the specimen. In such instances, the root-mean-square height may be a more accurate measure of the specimen height for density determinations. Another source of error in such a height measurement is that four measurements with the calipers may not provide enough data points to properly represent the true sample height, especially if the specimen is not a true right cylinder and/or if the ends thereof are irregular or sloped. Even if the operator uses extreme care and diligence in measuring the specimen height with the calipers, the calipers are not necessarily capable of properly measuring the irregular or uneven surfaces.

One widely used method of determining the bulk specific gravity of an asphalt mix specimen is by determining the mass to volume ratio of the specimen. Mass determinations are generally highly reliable through the use of state of the art balances and scales that are readily available in the marketplace. The volume measurement, however, is typically far less reliable than the mass determination. Several different methods of volume measurement incorporate the Archimedes' principal of water displacement. Another method of obtaining a volume measurement utilizes a dimensional analysis approach with calipers or micrometers.

The Archimedes' principal approximates the volume of a solid by determining the volume of water displaced by the solid when the solid is submerged in an adequately sized water bath. Generally, the ratio of the mass of water displaced to the specific gravity of the water is the resulting volume of the solid. However, in some instances, the determined volume may be adversely affected by water seeping into interconnected voids within the solid. In addition, the density of water is not constant and may be affected by temperature, impurities, or even an inconsistent water source. Consequently, the true volume of the solid may be an illusory quantity affecting the accuracy of the determined specific gravity and density of the solid, as well as the amount of water that is able to seep into the solid. However, another issue with the water displacement method is that submerging the sample in water is a destructive process. Though the sample may be dried after immersion, even very careful drying procedures do not typically provide repeatable specific gravity determination results for that sample in subsequent tests. The damage thus done to the specimen generally prohibits the use thereof in other material testing procedures.

Several AASHTO or ASTM standards utilize this water displacement principal in the determination of bulk specific gravity of compacted asphalt mixtures. However, basically all of these methodologies include inherent sources of error, typically depending on the conditions under which the procedures are performed. The saturated surface dry (SSD) method (AASHTO T166/ASTM D2726) tends to underestimate the volume of the specimen, thereby overestimating its bulk specific gravity or density. In order to overcome the limitations associated with the SSD method, techniques have been introduced that require coating the specimen with paraffin or parafilm (AASHTO T275/ASTM D1188), or vacuum sealing the specimen inside a plastic or poly-material bag(s) (ASTM D6752) as described, for example, in U.S. Pat. No. 6,321,589 to Regimand. However, these methods may overestimate the specimen volume by bridging the surface voids of the specimen, thus providing a resulting bulk specific gravity that is often lower than the true value of bulk specific gravity for that specimen. In addition, such methods may also require correction for the mass and volume of the coating or vacuum sealing bag, which may also introduce errors into the calculations.

The dimensional analysis method for determining the bulk specific gravity of the specimen approximates the volume by physically measuring the height and diameter dimensions of the specimen with calipers or micrometers. The specific gravity determined by the dimensional analysis method, however, is typically lower than the specific gravity determined by the water displacement method since dimensional analysis using calipers or a micrometer does not consider surface voids or other irregular surface features of the specimen.

In light of these limitations in being able to reliably determine the specimen height or other dimensions using existing technologies, there exists a need for a more reliable method for providing accurate dimensional values for a specimen. A method and/or apparatus is also needed that reduces the effect of operator judgment in determining specimen height or other dimensions so that single-laboratory and/or multi-laboratory variations do not affect the evaluations of the asphalt mix specimens. In addition, such an apparatus and/or method should be capable of nondestructively evaluating the specimen.

SUMMARY

The above and other needs are met by the subject matter disclosed herein which, in one embodiment, provides an apparatus adapted to determine a volume of a construction material sample. Such an apparatus comprises at least one sample-interacting device configured to interact with the construction material sample so as to determine at least one surface characteristic thereof. A computer device is configured to be capable of receiving the at least one surface characteristic from the at least one sample-interacting device, and to manipulate the at least one surface characteristic so as to form a three-dimensional representation of the construction material sample. The computer device is further configured to determine the volume of the construction material sample from the three-dimensional representation thereof.

Another aspect of the subject matter disclosed herein comprises an apparatus adapted to determine at least one dimension of a construction material sample having a plurality of dimensions. Such an apparatus includes a first portion of a sample holder operably engaged with at least one dimension-measuring device. A second portion of the sample holder is capable of being operably engaged with the first portion so as to allow the at least one dimension-measuring device to measure at least a first one of the dimensions of the construction material sample. The second portion is adapted to operably engage the construction material sample so as to hold the construction material sample within a coordinate system with respect to the first portion and the at least one dimension-measuring device. The second portion is further configured to be movable with the first portion and in registration with the coordinate system so as to allow the at least one dimension-measuring device to measure at least a second one of the dimensions of the construction material sample.

Still another aspect of the subject matter disclosed herein comprises an apparatus adapted to determine at least one dimension of a construction material sample. Such an apparatus comprises at least one sample-interacting device configured to interact with the construction material sample so as to determine at least one surface characteristic thereof. A computer device is configured to be capable of receiving the at least one surface characteristic from the at least one sample-interacting device, and to manipulate the at least one surface characteristic so as to determine the at least one dimension of the construction material sample.

Yet another aspect of the subject matter disclosed herein comprises a method of determining a volume of a construction material sample. Such a method includes determining at least one surface characteristic of a construction material with at least one sample-interacting device. Thereafter, the at least one surface characteristic is received from the at least one sample-interacting device at a computer device. The at least one surface characteristic is then manipulated with the computer device so as to form a three-dimensional representation of the construction material sample. The volume of the construction material sample is then determined, with the computer device, from the three-dimensional representation.

Still another aspect of the subject matter disclosed herein comprises a method of determining a volume of a construction material sample. Such a method includes first combining, with a computer device, a plurality of images of the construction material sample captured by at least one sample-imaging device so as to form a three-dimensional representation of the construction material sample. The volume of the construction material sample is then determined, with a computer device, from the three-dimensional representation.

Another aspect of the subject matter disclosed herein comprises a method of determining at least one dimension of a construction material sample. At least one surface characteristic of a construction material is determined with at least one sample-interacting device. The at least one surface characteristic is received from the at least one sample-interacting device at a computer device and manipulating the at least one surface characteristic with the computer device so as to determine, with the computer device, the at least one dimension of the construction material sample.

Another aspect of the subject matter disclosed herein comprises a method of measuring at least one dimension of a construction material sample having a plurality of dimensions, wherein the construction material sample is operably engaged with a second portion of a sample holder. The second portion of the sample holder is operably engaged with a first portion of a sample holder such that the construction material sample is within a coordinate system with respect to the first portion of the sample holder and at least one dimension-measuring device operably engaged therewith. At least a first one of the dimensions of the construction material sample is then measured with the at least one dimension-measuring device. The second portion is then moved with the first portion and in registration with the coordinate system, before at least a second one of the dimensions of the construction material sample is measured with the at least one dimension-measuring device.

The proposed methods and apparatuses thus eliminate the need for a destructive or otherwise sample-impairing testing method such as, for example, the Archimedes' water displacement methods. Whether an accurate height determination for the gamma ray attenuation method or an accurate volume determination for the dimensional analysis method is desired, the technology disclosed herein minimizes or eliminates the operator judgment and/or bias limitations previously discussed with respect to existing methods.

In some instances, the test method and apparatus for determining specimen height, shape, and/or volume can be applied to other general construction and/or paving-related materials such as loose soils and aggregates, portland cement, concrete cylinders, and many other applications. The improvement in volume, shape, and/or height measurement accuracy and/or definition will, in turn, provide for more reliable density and specific gravity determinations. Thus, a subsequent effect will be improved design, quality control, and quality assurance of construction and/or paving related materials. Further benefits may include, for example, ultimately improved structures and a reduction in disputes between owner and contractor that result from the uncertainty of test results. Thus, embodiments of the subject matter disclosed herein provide significant advantages as disclosed, described, and further detailed herein.

BRIEF DESCRIPTION OF THE DRAWINGS

The subject matter described herein will now be explained with reference to the accompanying drawings of which.

DETAILED DESCRIPTION

The present subject matter will be described more fully hereinafter with reference to the accompanying drawings, in which some, but not all embodiments of the subject matter disclosed herein are shown. Indeed, the subject matter disclosed herein may be embodied in many different forms and should not be construed as limited to the embodiments set forth herein; rather, these embodiments are provided so that this disclosure will satisfy applicable legal requirements. Like numbers refer to like elements throughout.

Figure 1A:
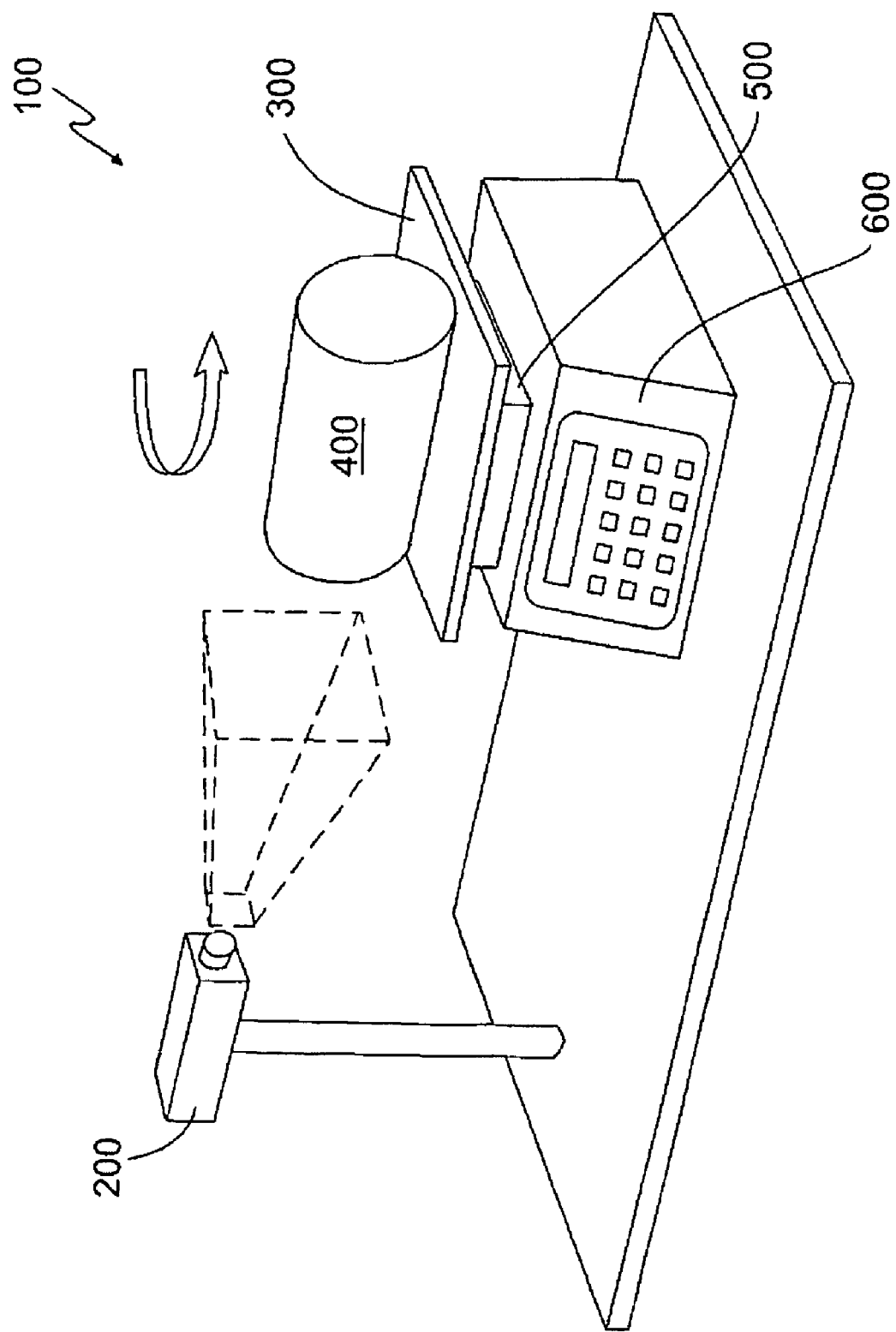
FIGS. 1A and 1B are schematics of an apparatus for determining at least one surface characteristic of a construction material sample, implementing a single sample-interacting device, according to one embodiment of the subject matter disclosed herein.
Figure 1B:
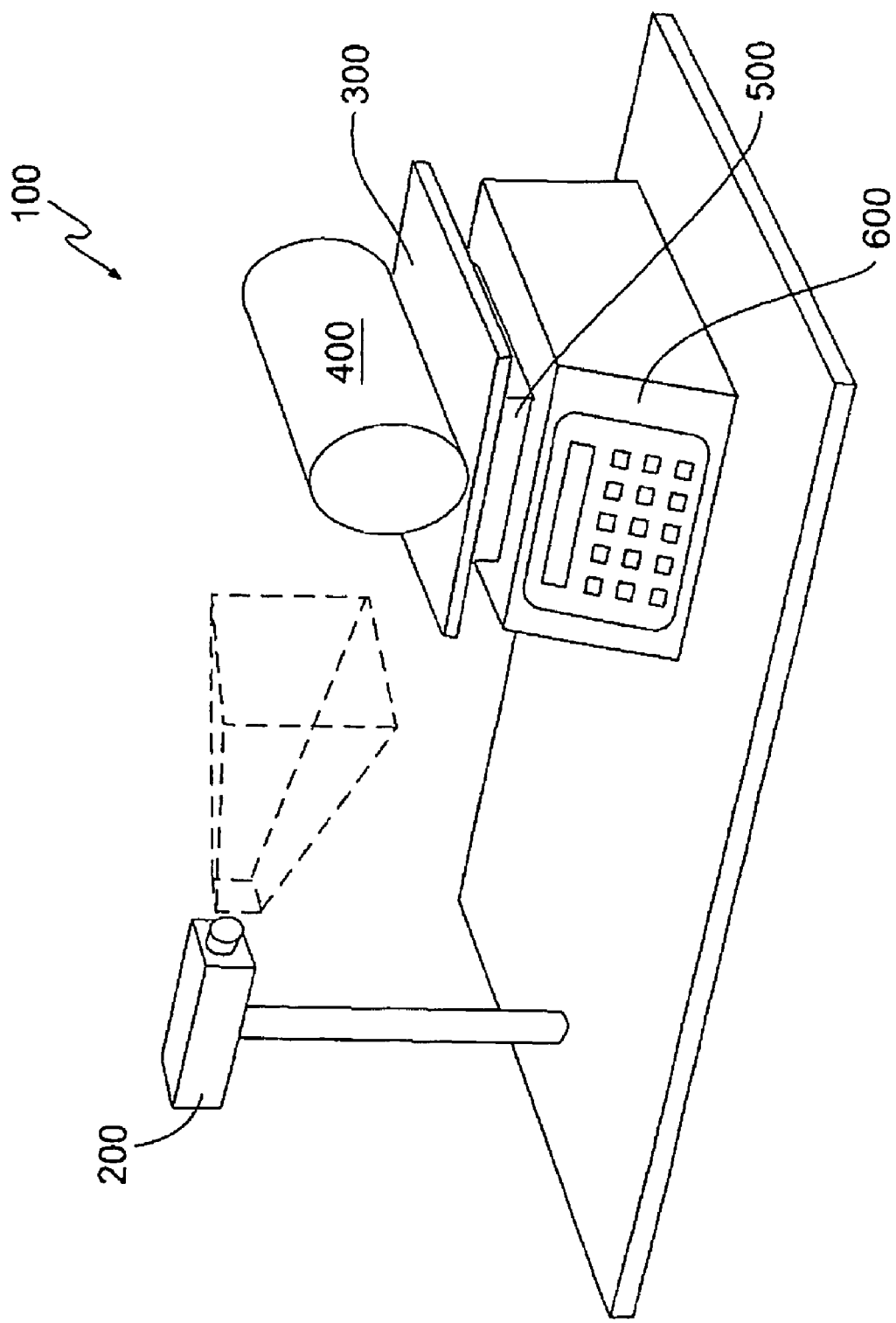

FIGS. 1A and 1B illustrate an apparatus adapted to determine at least one surface characteristic of a construction and/or paving-related material sample according to one embodiment of the subject matter disclosed herein, the apparatus being indicated generally by the numeral 100. Apparatus 100 includes at least one sample-interacting device (or material-interacting device) 200 and a sample holder 300 configured to be capable of supporting a sample 400 of a paving-related material or other construction material. Note that the term "paving-related material" as used herein refers to, for example, uncompacted bituminous paving mixtures, loose soils and aggregates, as well as field cores and laboratory prepared specimens of compacted bituminous paving material, while the term "construction material" as used herein is more general and includes, for example, paving-related materials, portland cement, concrete cylinders, and the like.

Sample-interacting device 200 may use, for example, a point source, a line source, or a wave source to provide, for instance, light, sound, ultrasound, radiation, physical contact, and/or other medium for allowing at least one surface characteristic of sample 400 to be determined. One skilled in the art will appreciate that such a device 200 may be appropriately configured to use the light, sound, ultrasound, radiation (including, for example, microwave radiation or infrared radiation), physical contact and/or other medium to perform, for example, a measurement of at least one surface characteristic, such as a dimension, of sample 400 using, for instance, a reflectance methodology, a transmission methodology, a duration methodology, a contact methodology, or any other suitable methodology, wherein device 200 may include, for example, at least one corresponding and appropriate emitter/detector pair, or appropriate sensors, for measuring the at least one surface characteristic. For instance, device 200 may be configured to use structured light, laser range finders, or x-rays for non-contact-type measurements; linear variable differential transformers (LVDT) or other physical mechanisms for contact-type measurements; or any other suitable measuring technology. For example, an optical methodology or a photographic methodology such as, for instance, stereo-vision techniques, may be used for performing 3D profiling. Various imaging devices such as scanners or cameras may also be suitable in this regard where the appropriate determination of a surface characteristic(s), such as a dimension, may be accomplished by associated software or image processing procedure executed on a computer device 600 associated with sample-interacting device(s) 200. In some instances, device 200 may comprise, for example, a three-dimensional profiler device such as that made by, for instance, Shape Grabber, Inc. of Ottawa, Ontario, Canada or National Optics Institute of Sainte-Foy, Quebec, Canada. However, one skilled in the art will appreciate that many other sample-interacting devices may be implemented within the spirit and scope of the subject matter disclosed herein.

Sample holder 300 is configured to hold sample 400 with respect to sample-interacting device 200 so as to allow sample-interacting device 200 to determine the appropriate surface characteristic(s) of sample 400. Such a surface characteristic may include, for example, a dimension, a texture, a roughness, or other identifiable surface aspect of sample 400, including identification and/or quantification of voids, irregularities, or other features of the sample surface. In certain situations, sample-interacting device 200 may be configured such that the necessary or desired surface characteristic(s) of sample 400 can be determined with sample 400 held in one position by sample holder 300. However, in instances, where sample 400 has a complex three-dimensional configuration, an appropriate determination or measurement may not be possible with sample 400 in a single position with respect to sample-interacting device 200. Accordingly, in instances where a second determination or measurement is necessary or desirable to produce an accurate representation of, for example, the dimensional measurement(s) of sample 400, sample 400 may be moved from a first position to a second position with respect to sample holder 300 for the second measurement. However, significant inaccuracies may be introduced if sample 400 is moved since a common reference point with respect to sample 400 by which the two measurements must be coordinated may be lacking. Further, in other instances, sample 400 may be irregularly shaped or, in the case of aggregates, soils, sands, or the like, configured such that it may be inconvenient or otherwise not practically possible to hold sample 400 with respect to sample-interacting device 200, or move sample 400 to another position, to allow the appropriate dimension(s) of sample 400 to be measured.

Accordingly, one advantageous aspect of the subject matter disclosed herein in this regard is the implementation of a computer analysis device 600 capable of executing a software package for analyzing the surface characteristic(s) of sample 400 determined by at least one sample-interacting device 200 in order to extract desired information, while overcoming some of the inaccuracies encountered in obtaining a three-dimensional representation of a sample. For example, engineering/modeling/reverse engineering software such as, for instance, ProEngineer, Matlab, Geomagic Studio, or other appropriate package being executed by computer device 600, can be configured to receive the at least one surface characteristic determined by sample-interacting device 200. For instance, sample-interacting device 200 using a point source of light may be configured to detect the behavior of the light interacting with sample 400, wherein the detected light may be indicative of coordinates or distances of each of the measured points on sample 400 with respect to sample-interacting device 200. Accordingly, an increased number of measurements of sample 400 with such a point source, and the proximity of subsequent measurements to previous measurements may directly affect the resolution of the representation of sample 400 obtained from that process. That is, a dense "point cloud" may provide a significantly higher resolution of the surface characteristic(s) of sample 400 as compared to very few point measurements distributed across the surface of sample 400. However, the resolution necessary to obtain appropriate and valid results of the at least one surface characteristic of sample 400 is not limited hereby in any manner and one skilled in art will appreciate that such resolution is a matter of choice associated with the desired result to be achieved.

Figure 2A:
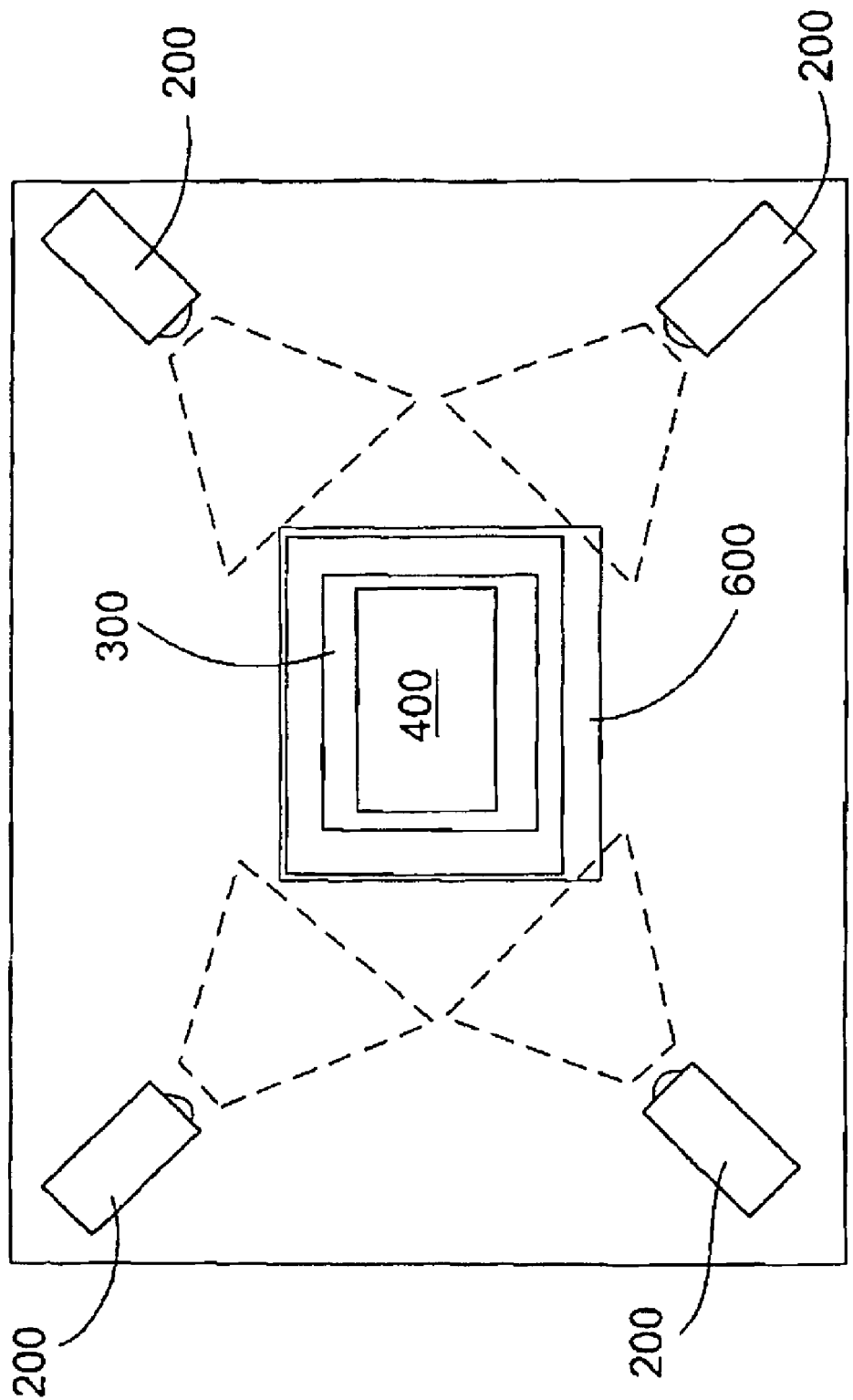
FIG. 2A is a schematic of an apparatus for determining at least one surface characteristic of a construction material sample, implementing a plurality of sample-interacting devices, according to one embodiment of the subject matter disclosed herein.

FIGS. 1A and 1B further illustrate sample 400 being moved with respect to sample-interacting device 200 about a vertical axis defined by sample holder 300, wherein such movement may be accomplished manually (by the operator physically rotating the sample 400 on the sample holder 300) or in an automated manner such as by a motorized or mechanized system associated with and for rotating sample holder 300 so as to rotate sample 400. In other instances, sample 400 may be stationary and sample-interacting device 200 moved around sample 400. In still other instances, as shown in FIG. 2A, a plurality of sample-interacting devices 200 may be implemented such that moving either sample 400 or sample-interacting device(s) 200 may not be necessary in order to determine or capture the desired surface characteristic(s) of sample 400. One skilled in the art will also appreciate that, in some instances, that a sample holder 300 may not be a positive aspect of apparatus 100. That is, in some instances, sample 400 may be, for example, supported by at least one sample-interacting device 200, whereby at least one sample-interacting device 200 is configured to determine the desired surface characteristic(s) of sample 400 while providing support therefor. In other instances, sample-interacting device(s) 200 may be configured to act upon a sample 400 in situ and, as such, does not require a sample holder 300 for supporting sample 400. More particularly, for example, ASTM E 965 is a standard for determining the surface texture of a roadway and involves spreading a calibrated sand on the roadway and then spreading that sand out across the roadway until a dispersed condition is met. The diameter of the sand patch is then measured, whereby the area of the sand patch and the known density of the calibrated sand may be used to determine the surface roughness of the roadway. According to embodiments of the subject matter disclosed herein may be used to determine surface roughness by implementing a sample-interacting device 200 configured to be moved relative to the roadway so as to interact with sample 400 in situ, thereby obviating the need for a sample holder 300 per se. the surface characteristic(s) determined by sample-interacting device 200 would then be transferred to computer device 600 to determine the nature of the surface characteristic(s) and thus at least one dimension of sample 400 (in this instance, the distance between sample-interacting device 200 and sample 400 can be indicative of the texture of the surface of sample 400 and thus an average separation distance can be determined, wherein the average separation distance may be related to, for example, the thickness of the roadway in that area).

Figure 3A:
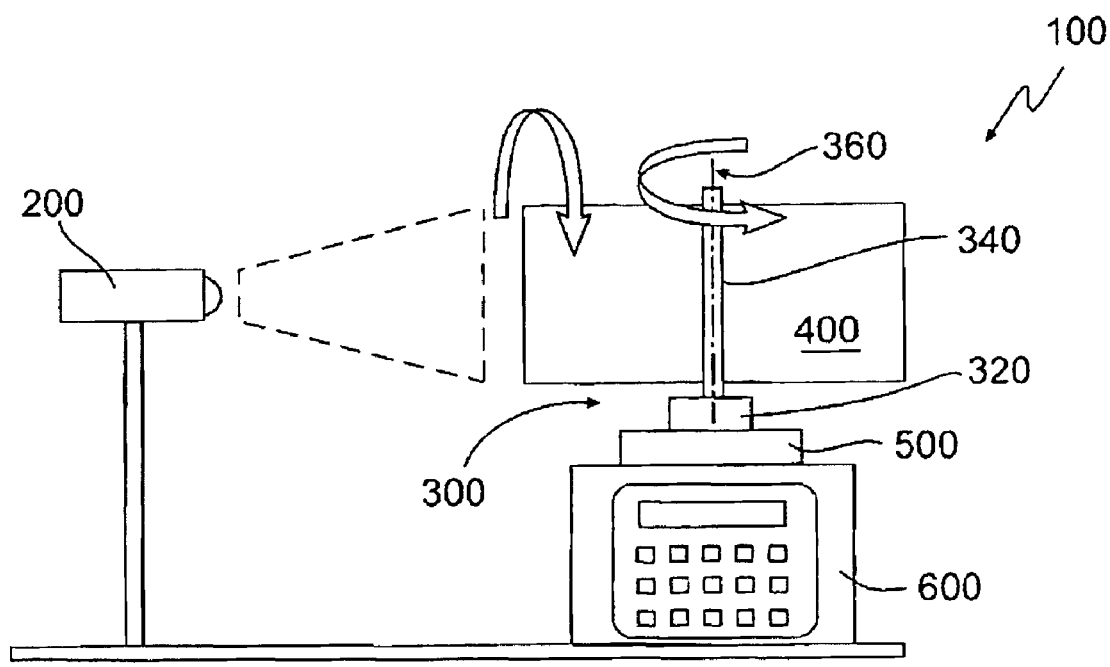
FIGS. 3A and 3B are schematics of an apparatus for determining at least one dimension of a construction material sample, implementing a dimension-measuring device, according to one embodiment of the subject matter disclosed herein.
Figure 3B:
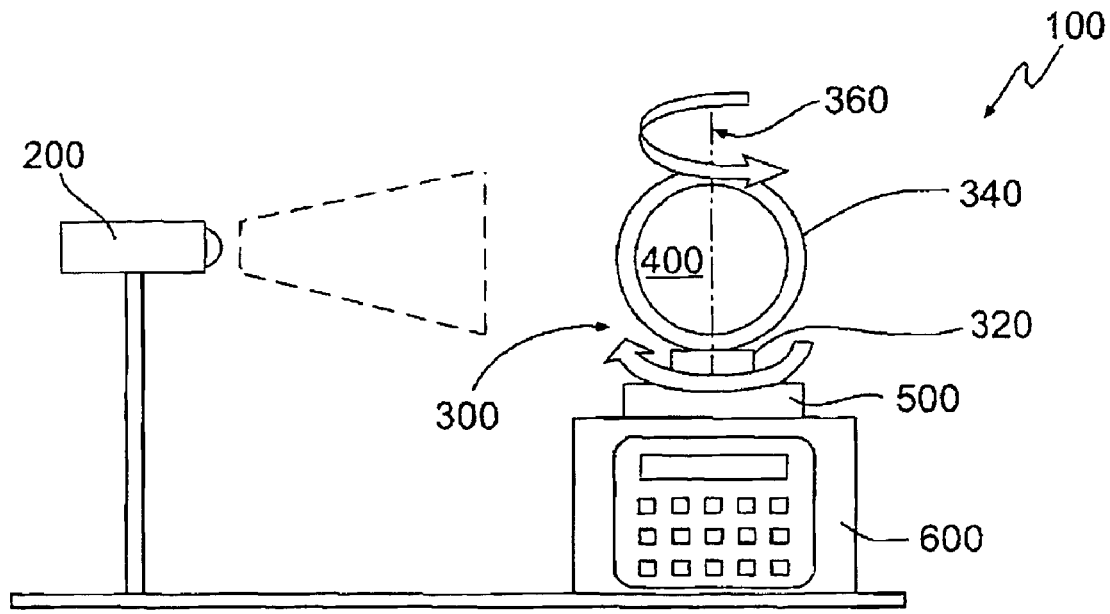

In an alternate embodiment of the subject matter disclosed herein, as shown in FIGS. 3A and 3B, sample holder 300 may be configured with a first portion 320 and a second portion 340, wherein first and second portions 320, 340 are configured to cooperate to hold sample 400 such that appropriate dimension or other measurement(s) can be determined by a dimension-measuring device (as one form of a sample-interacting device 200). That is, in one embodiment, first portion 320 may be disposed at a selected position with respect to sample-interacting device 200. Second portion 340 may then be affixed to sample 400 before second portion 340 is interfaced with first portion 320 in an appropriate manner. For example, first portion 320 may define a keyway (not shown) configured to receive a key (not shown) protruding from second portion 340 such that, when interfaced, the first and second portions 320, 340 will hold sample 400 in a known position with respect to sample-interacting device 200. In any instance, first and second portions 320, 340 are configured so as to define a coordinate system with respect to sample-interacting device 200. That is, when second portion 340 is interfaced with first portion 320, sample 400 is located within a coordinate system recognized by sample-interacting device 200. In other instances, first and second portions 320,340 may be used by an appropriate software analysis package being executed by a computer device 600, as previously described, to define a coordinate system for analyzing sample 400.

In one example, if sample 400 comprises a generally cylindrical compacted field core, second portion 340 of sample holder 300 may be configured as a ring wrapping about the circumference of sample 400. Accordingly, first portion 320 of sample holder 300 may be configured to receive second portion 340 such that the axis of sample 400 is generally horizontal. In such a configuration, second portion 340 may be rotated with respect to first portion 320 between measurements by sample-interacting device 200 such that the sample 400 is caused to rotate about its axis. In other instances, for example, where sample 400 comprises an aggregate, sample holder 300 may be configured as, for instance, one or more screens 380 for supporting the aggregate (for example, two opposing screens 380 having the aggregate retained therebetween) with respect to sample-interacting device 200 so as to allow the appropriate dimensions or other surface characteristics of the components of the aggregate to be measured as shown, for example, in FIG. 4. As such, one skilled in the art will appreciate that embodiments of the subject matter disclosed herein may be useful to determine the dimensions or other surface characteristics of many different configurations of samples 400 and thus may be used for such purposes as, for example, determining the volume of a cylindrical compacted field core, modeling the roughness or texture of a surface, or gradating components of an asphalt paving mix or aggregate.

Once a first measurement of sample 400 in a first position is performed by sample-interacting device 200, sample 400 can then be moved to a second position to allow a second measurement of sample 400 to be performed, where such measurements may be associated with, for example, a dimension of sample 400. In such a manner, a more accurate determination of the appropriate surface characteristic(s) of sample 400 can be made so as to enable, for example, the volume of sample 400 to be more closely and accurately determined. Accordingly, in one embodiment as shown in FIGS. 3A and 3B, first and second portions 320, 340 of sample holder 300 define a vertical axis 360 and first and second portions 320, 340 are configured so as to be able to rotate about axis 360 between measurements by sample-interacting device 200. FIGS. 3A and 3B further show sample 400 rotating around axis 360. For example, first and second portions 320, 340 may be configured to rotate in 90 degree increments or 180 degree increments (or any suitable degree increment or even in a continuous sweep) between measurements by sample-interacting device 200, while maintaining sample 400 within the established coordinate system. That is, first and second portions 320, 340 may be configured such that, for instance, a reference point is maintained on first portion 320, second portion 340, and/or sample 400 as sample 400 is rotated about axis 360. Thus, subsequent analysis of the resulting data can use the common reference point in order to reconcile the measured surface characteristic(s) from the particular view of each measurement. Further, multiple measurements of sample 400 from multiple views will also provide redundant data useful for verifying accuracy of the determined surface characteristic(s) of sample 400, thereby providing another significant advantage of embodiments of the subject matter disclosed herein. In some instances, sample-interacting device(s) 200 may be used to perform repeated measurements of sample 400 such that an average of those measurements is used in subsequent analyses of the data. The use of such averages may, in some instances, provide a more accurate representation of the surface characteristic of sample 400 as compared to a single measurement.

Figure 4:
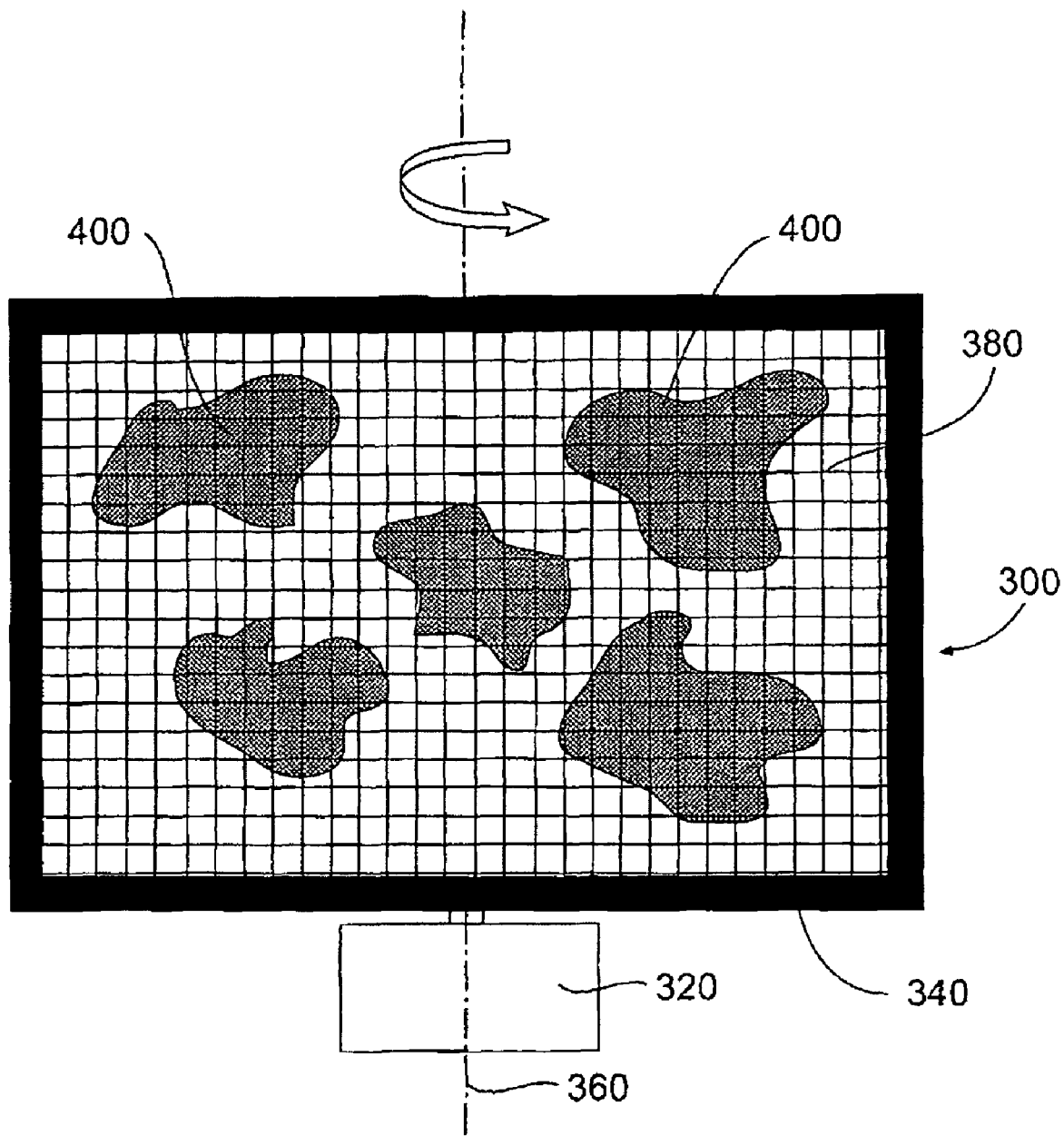
FIG. 4 is a schematic of an alternate sample holder for an apparatus for determining at least one dimension of a construction material sample, according to one embodiment of the subject matter disclosed herein.

In light of the relationship of sample-interacting device 200 to sample 400, as shown in FIGS. 3A, 3B, and 4, other embodiments of the subject matter disclosed herein may be configured such that first and second portions 320, 340 hold sample 400 stationary, while sample-interacting device 200 is configured to move about sample 400 so as to perform the appropriate measurements. In still other instances, both sample-interacting device 200 and sample holder 300 may be movable with respect to each other, or mirrors may be used to enable sample-interacting device 200 to interact with sample 400. Further, other embodiments of the subject matter disclosed herein may have sample holder 300 configured such that second portion 340 is movable with respect to first portion 320 where, for example, first portion 320 may be stationarily disposed with respect to sample-interacting device 200. For a sample holder 300 configured in such a manner, second portion 340 holding sample 400 may be movable in many different manners with respect to first portion 320, as will be appreciated by one skilled in the art. In any instance, such embodiments of apparatus 100 are configured such that sample 400 is maintained in registration with the coordinate system through any movement of sample-interacting device 200 and/or first and/or second portions 320, 340 of sample holder 300.

Figure 2B:
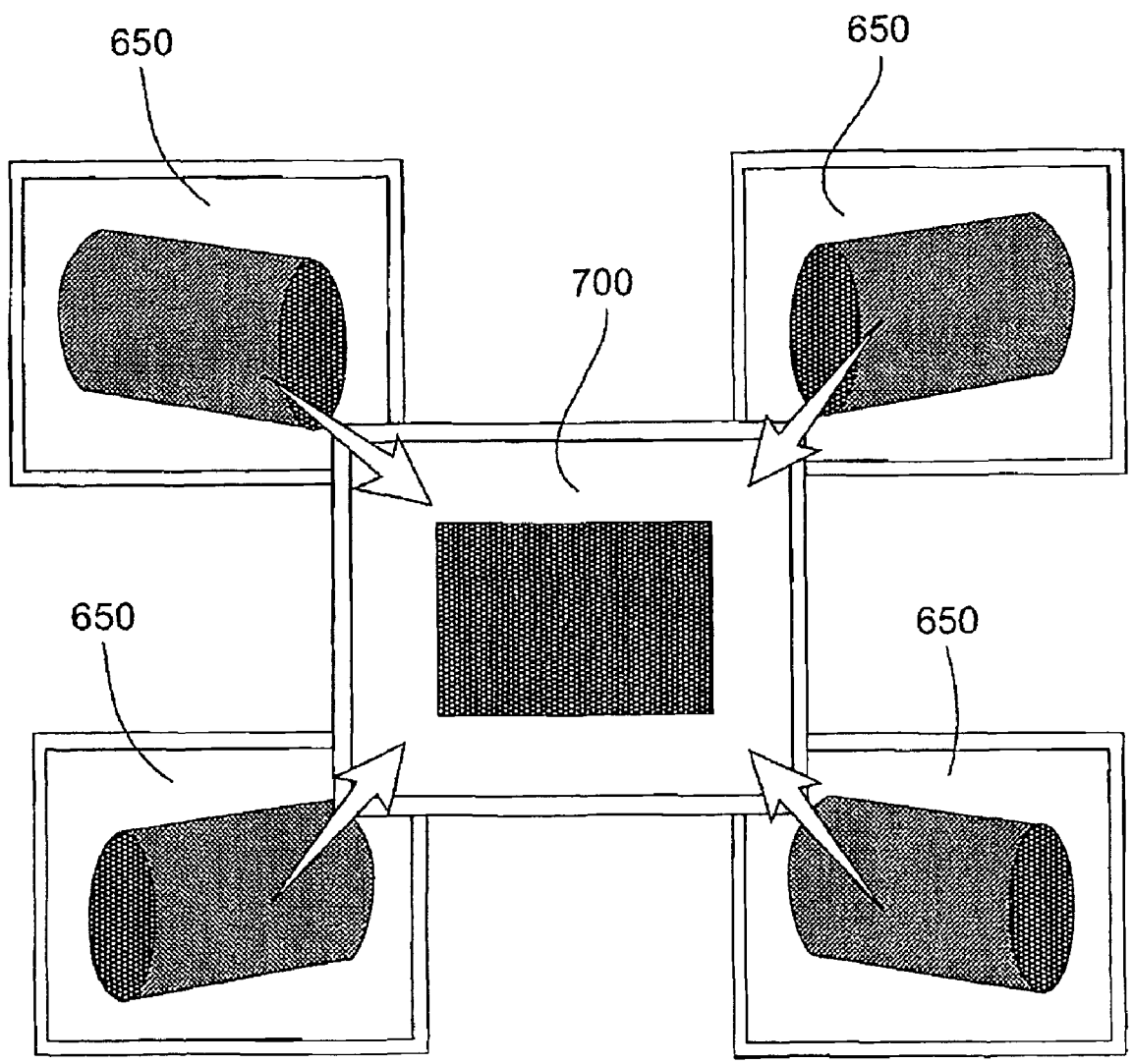
FIG. 2B is a schematic of a plurality of surface characteristics, in the form of images of the construction material sample, determined by the plurality of sample-interacting devices shown in FIG. 2A, and a three-dimensional representation of the construction material sample formed by combining the images, from which a volume of the construction material sample can be obtained, according to one embodiment of the subject matter disclosed herein.

In any case, multiple views and/or measurements or other determinations of the surface characteristic(s) of sample 400 may result in a plurality of representations of sample 400 from different perspectives, wherein the views and/or measurements must then be combined in order to provide coherent and useful results. Where sample 400 and/or sample-interacting device 200 must be moved, or multiple perspectives of sample 400 are obtained, in order to provide three-dimensional surface characteristics of sample 400, the software executed by computer device 600, in cooperation with sample-interacting device 200, may be configured to determine a coordinate system or other frame of reference for the various measurements or determinations of the surface characteristic(s) of sample 400 performed by sample-interacting device 200. For example, the frame of reference may be designated, for example, at least partially according to sample holder 300 or according to a surface aspect or feature of sample 400, such as a void or other irregularity. In other instances, the frame of reference may be artificial, such as a mark or other removable (or inconsequential) surface feature added to sample 400 prior to exposure to sample-interacting device 200. As such, once a sufficient number of source-associated measurements have been executed, the various perspectives 650 of sample 400 obtained by sample-interacting device(s) 200, as shown in FIG. 2B (where FIG. 2B illustrates the plurality of perspectives of the sample 400 captured by the corresponding plurality of sample-interacting devices 200 shown in FIG. 2A), can be combined or "stitched together" according to the coordinate system or other frame of reference into a single three-dimensional representation or model 700 of sample 400.

One skilled in the art will thus appreciate that apparatus 100 may be configured in many different manners in addition to that described herein. For example, apparatus 100 may include multiple sample-interacting or dimension-measuring devices 200, each disposed so provide different perspectives of the sample 400, or one or more sample-interacting devices 200 may each include multiple sources and/or detectors. In addition, various other mechanisms, such as mirrors, could be implemented to facilitate the determination of the desired surface characteristic(s) of sample 400. Thus, the embodiments disclosed herein are provided for example only and are not intended to be limiting, restrictive, or inclusive with respect to the range of contemplated configurations of the subject matter disclosed herein.

According to a further advantageous aspect of the subject matter disclosed herein, apparatus 100 may also be configured such that sample-interacting device 200 and/or computer device 600 is capable of determining the volume of sample 400. One value often associated with the determination of the volume of sample 400 is the density thereof. As previously described, the general procedures heretofore implemented by recognized standards in the construction industry are often, for instance, cumbersome, inaccurate, or destructive to sample 400. As such, in some instances, embodiments of the subject matter disclosed herein may also include a mass-determining device 500 operably engaged with sample holder 300 such that, as the volume of the sample 400 is being determined by the sample-interacting device 200, mass of the sample 400 can also be determined concurrently. The density of sample 400 can thereby be expeditiously determined with minimal handling of the sample 400. Such a mass-determining device 500 may comprise, for example, a load cell or other suitable device as will be appreciated by one skilled in the art. In still other instances, it may also be advantageous for the determination of the volume and/or the density of sample 400 by the apparatus 100 to be at least partially automated so as to reduce the subjectivity of handling by an operator. Accordingly, in such instances, apparatus 100 may also include a computer device 600 operably engaged with the sample-interacting device 200, mass-determining device 500, and/or sample holder 300. Such a computer device 600 may be configured to, for instance, verify that sample 400 is properly placed with respect to sample holder 300 and/or the sample-interacting device 200, coordinate the movement of sample 400 with the measurements performed by sample-interacting device 200, determine the mass of sample 400 from mass-determining device 500, and compute the density of sample 400 all in one automated procedure. Computer device 600 may also be configured to perform other procedures on the collected sample data that may be of further interest. For example, computer device 600 may be configured to compute the volume of sample 400 from a complex integration of a three-dimensional surface image of the sample 400 and/or may be configured to determine an actual volume of the sample 400 by determining the effect of surface voids or roughness in sample 400. Computer device 600 may also vary in complexity depending on the computational requirements of apparatus 100. For example, an image-intensive apparatus 100 using a plurality of sample-interacting devices 200 may require a significant capacity and an image-capable computer device 600, while a less complex dimension-determining may require less computational capacity and, in light of such requirements, an appropriate computer device 600 is provided. Thus, one skilled in the art will appreciate that embodiments of the apparatus 100 may be used for many other forms of sample analysis in addition to those discussed herein.

Many modifications and other embodiments of the subject matter disclosed herein will come to mind to one skilled in the art to which the subject matter disclosed herein pertains having the benefit of the teachings presented in the foregoing descriptions and the associated drawings. For example, one skilled in the art will appreciate that the apparatus and method as disclosed and described herein, in addition to providing an alternative to the density determination methodology outlined in the applicable density standards, may also be implemented within the methodology of other higher-level standards that call, for instance, for the determination of sample density using those density standards, or for the determination of sample dimensions such as, for example, a histogram of aggregate sizes. For example, several AASHTO/ASTM standards are directed to aggregate gradation and may specify the determination of an aggregate size histogram, wherein the apparatus and method as disclosed and described herein may be implemented to make that determination. Such standards include, for instance:

AASHTO T 27 Sieve Analysis of Fine and Coarse Aggregates;

AASHTO T 30 Mechanical Analysis of Extracted Aggregate;

AASHTO MP 2 Standard Specification for SUPERPAVE Volumetric Mix Design;

AASHTO T 312 Method for Preparing and Determining the Density or HMA Specimens by Means of the SHRP Gyratory Compactor;

ASTM C 136 Sieve Analysis of Fine and Coarse Aggregates;

ASTM D 5444 Test Method for Mechanical Size Analysis of Extracted Aggregate;

ASTM D 3398 Test Method for Index of Aggregate Particle Shape and Texture;

ASTM D 2940 Specification for Graded Aggregate Material For Bases or Subbases for Highways or Airports;

ASTM D 448 Classification for Sizes of Aggregate for Road and Bridge Construction; and ASTM D 1139 Standard Specification for Aggregate for Single and Multiple Bituminous Surface Treatments.

Note that such a list is merely exemplary of some standards for aggregates in which aggregate gradation may be specified, and is not intended to be limiting, restrictive, or inclusive with respect to such higher-level standards which may specify a dimension, volume, density, and/or other sample property determination that may be accomplished using the apparatus and method as disclosed and described herein. Accordingly, additional embodiments of the subject matter disclosed herein may be directed to such higher level methods implementing the apparatus and method as disclosed herein. Further, other additional embodiments of the subject matter disclosed herein may, for example, be used to determine the texture of a sample. Some examples of ASTM standards requiring an examination of the sample texture, wherein the apparatus and method as disclosed and described herein may also be implemented to make that determination, include:

ASTM E 965 Standard Test Method for Measuring Pavement Macro Texture Depth Using a Volumetric Technique;

ASTM E 1274 Standard Test Method for Measuring Pavement Roughness Using a Profilograph; and ASTM E 2157 Standard Test Method for Measuring Pavement Macro Texture Properties Using the Circular Track Method.

Therefore, it is to be understood that the subject matter disclosed herein is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus adapted to determine at least one macroscopic surface characteristic of a roadway surface material, said apparatus comprising:
   at least one material-interacting device and computer device configured to:
   (a) interact with the roadway surface material in situ for determining at least one surface dimension measurement thereof; and
   (b) manipulate the at least one surface dimension measurement so as to determine at least one of a macro texture characteristic and a micro texture characteristic of the roadway surface material,
   wherein the at least one material-interacting device is configured to determine the at least one surface dimension measurement of the roadway material using a light for interacting with the roadway surface material and the computer device is configured to be capable of determining a representative surface dimension from a plurality of the at least one surface dimension measurement;
   wherein the roadway surface material is an exposed surface.

2. An apparatus according to claim 1 wherein the at least one material-interacting device is configured to determine the at least one of a macro texture characteristic and a micro texture characteristic of the roadway surface material using at least one of sound, ultrasound, light, and radiation for interacting with the roadway surface material.

3. An apparatus according to claim 1 wherein the at least one sample-interacting device further comprises at least one sample-imaging device and the at least a macro texture characteristic and a micro texture characteristic further comprises at least a partial image of the roadway surface material.

4. An apparatus according to claim 1 wherein the at least one material-interacting device comprises at least one of a profiler device and a material-imaging device.

5. An apparatus according to claim 1 wherein the at least one material-interacting device is configured to interact with the roadway surface material without contacting the roadway surface material to determine the at least one measurement thereof.

6. An apparatus according to claim 1 wherein the computer device is configured to determine a measure of any of a surface void, a surface irregularity, a surface dimension, a surface coordinate, texture, a surface feature, a shape feature, a length, a depth, volume, an area, height, thickness, and angularity.

7. An apparatus according to claim 1 wherein the computer device is configured to be capable of determining at least one of a texture and a roughness of the roadway surface material from the at least one measurement determined by the at least one material-interacting device.

8. An apparatus according to claim 1 wherein the at least one of a macro texture characteristic and a micro texture characteristic is a mean texture depth characteristic of the roadway surface material.

9. An apparatus according to claim 1 wherein the at least one of a macro texture characteristic and a micro texture characteristic is a root mean square depth characteristic of the roadway surface material.

10. An apparatus according to claim 1 wherein the at least one of a macro texture characteristic and a micro texture characteristic is a mean profile depth characteristic of the roadway surface material.

11. An apparatus according to claim 1 wherein the at least one material-interacting device comprises a laser configured to generate light to interact with the roadway surface material for determining at least one measurement thereof.

12. An apparatus according to claim 1 wherein the at least one material-interacting device comprises an optical system configured to receive light that has interacted with the roadway surface material for determining at least one measurement thereof.

13. An apparatus according to claim 12 wherein the optical system is configured to utilize a stereo-vision technique for determining the at least one measurement of the roadway surface material.

14. An apparatus according to claim 1 wherein the at least one of a macro texture characteristic and a micro texture characteristic is a transformation between a mean texture depth and a mean profile depth of the roadway surface material.

15. An apparatus according to claim 1 wherein the at least one of a macro texture characteristic and a micro texture characteristic comprises at least one of a dimension, a texture, a roughness, a void identification, a void quantification, an irregularity identification, and an irregularity quantification.

16. A method of determining at least one macroscopic surface characteristic of a roadway surface material, comprising:
    interacting with the roadway surface material in situ with at least one material-interacting device for determining at least one surface dimension measurement thereof;
    manipulating the at least one surface dimension measurement for determining at least one of a macro texture characteristic and a micro texture characteristic of the roadway surface material;
    using a light to interact with the roadway surface material for determining the at least one of a macro texture characteristic and a micro texture characteristic of the roadway surface material; and
    determining a representative surface dimension from a plurality of the at least one surface dimension measurement;
    wherein the roadway surface material is an exposed surface.

17. A method according to claim 16 wherein determining at least one of a macro texture characteristic and a micro texture characteristic of the roadway surface material sample further comprises determining at least a texture characteristic of the roadway surface material sample with at least one sample-interacting device using at least one of sound, ultrasound, light, and radiation.

18. A method according to claim 16 wherein determining at least one measurement of the roadway surface material comprises determining the at least one measurement of the roadway surface material with at least one material-interacting device comprising at least one of a profiler device and a material-imaging device.

19. A method according to claim 16 wherein determining at least one measurement of the roadway surface material comprises determining at least a partial image of the roadway surface material with at least one material-imaging device.

20. A method according to claim 16 wherein determining at least one measurement of the roadway surface material comprises determining the at least one measurement of the roadway surface material without contacting the at least one material-interacting device with the roadway surface material.

21. A method according to claim 16 further comprising determining a measure of any of a surface void, a surface irregularity, a surface dimension, a surface coordinate, texture, a surface feature, a shape feature, a length, a depth, volume, an area, height, thickness, and angularity.

22. A method according to claim 16 comprising determining at least one of a texture and a roughness of the roadway surface material from the at least one measurement determined by at least one material-interacting device.

23. A method according to claim 16 wherein the at least a texture characteristic is a root mean square depth characteristic of the roadway surface material.

24. A method according to claim 16 wherein the at least one of a macro texture characteristic and a micro texture characteristic is a transformation between a mean texture depth and a mean profile depth of the roadway surface material.

25. A method according to claim 16 wherein the at least one of a macro texture characteristic and a micro texture characteristic is a mean texture depth characteristic of the roadway surface material.

26. A method according to claim 16 wherein the at least one of a macro texture characteristic and a micro texture characteristic is a mean profile depth characteristic of the roadway surface material.

27. A method according to claim 16 comprising utilizing a laser to generate light for determining the at least one measurement.

28. A method according to claim 16 wherein the at least one of a macro texture characteristic and a micro texture characteristic comprises at least one of a dimension, a texture, a roughness, a void identification, a void quantification, an irregularity identification, and an irregularity quantification.

29. An apparatus adapted to determine at least one macroscopic surface characteristic of a roadway surface material, said apparatus comprising:

> at least one material-interacting device configured to be moved relative to the roadway surface material and computer device configured to:
> (a) interact with the roadway surface material in situ for determining at least one surface dimension measurement thereof; and
> (b) manipulate the at least one surface dimension measurement so as to determine at least a macro surface characteristic of the roadway surface material,
> wherein the at least one material-interacting device is configured to determine the at least one of a macro texture characteristic and a micro texture characteristic of the roadway surface material using at least one of sound, ultrasound, light, physical contact, and radiation for interacting with the roadway surface material and the computer device is configured to be capable of determining a representative surface dimension from a plurality of the at least one surface dimension measurement;
> wherein the roadway surface material is an exposed surface.

30. An apparatus according to claim 29 wherein the at least one of a macro surface characteristic comprises a texture.

31. A method of determining at least one macroscopic surface characteristic of a roadway surface material, comprising:

> interacting with the roadway surface material in situ with at least one material-interacting device for determining at least one surface dimension measurement thereof; and
> manipulating the at least one surface dimension measurement for determining at least one of a macro texture characteristic and a micro texture characteristic of the roadway surface material with at least one sample-interacting device using at least one of sound, ultrasound, light, physical contact, and radiation and determining a representative surface dimension from a plurality of the at least one surface dimension measurement;
> wherein the roadway surface material is an exposed surface.

32. A method according to claim 31 wherein the at least one of a macro surface characteristic and a micro surface characteristic comprises a texture.

33. The method according to claim 31, wherein interacting with the roadway surface material comprises interacting with the roadway surface material with at least one material-interacting device in a first position relative to the roadway surface material and in a second position relative to the roadway surface material in which the material-interacting device is moved about the roadway surface material from the first position to the second position.

34. The method according to claim 31, wherein interacting with the roadway surface material comprises interacting with the roadway surface material with at least one light source in a first position relative to the roadway surface material and in a second position relative to the roadway surface material in which the light source is moved about the roadway surface material from the first position to the second position.

35. An apparatus adapted to determine at least one macroscopic surface characteristic of a roadway surface material, said apparatus comprising:

> at least one material-interacting device configured to be movable relative to the roadway surface material and computer device configured to:
> (a) interact with the roadway surface material in situ for determining at least one surface dimension measurement thereof;
> (b) manipulate the at least one measurement so as to determine at least a macro texture characteristic of the roadway surface material; and
> (c) determine a representative surface dimension from a plurality of the at least one surface dimension measurement;
> wherein the roadway surface material is an exposed surface.

36. The apparatus according to claim 35, wherein the computer device is configured to be capable of determining at least one of a texture and a roughness of the roadway surface material from the at least one measurement determined by the at least one material-interacting device.

* * * * *